US009669021B2

(12) United States Patent
Giovinazzo et al.

(10) Patent No.: US 9,669,021 B2
(45) Date of Patent: *Jun. 6, 2017

(54) SUBLINGUAL APOMORPHINE

(71) Applicant: Sunovion Pharmaceuticals Inc., Marlborough, MA (US)

(72) Inventors: Anthony John Giovinazzo, Caledon (CA); David Bruce Hedden, Ann Arbor, MI (US); Marc L. De Somer, Winchester, MA (US); Nathan John Bryson, Toronto (CA)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/971,532

(22) Filed: Dec. 16, 2015

(65) Prior Publication Data
US 2016/0101101 A1  Apr. 14, 2016

Related U.S. Application Data

(60) Continuation of application No. 14/684,146, filed on Apr. 10, 2015, now Pat. No. 9,326,981, which is a division of application No. 12/813,820, filed on Jun. 11, 2010, now Pat. No. 9,044,475.

(60) Provisional application No. 61/186,445, filed on Jun. 12, 2009.

(51) Int. Cl.
| | | |
|---|---|---|
| A61F 13/00 | (2006.01) |
| A61K 31/485 | (2006.01) |
| A61K 9/00 | (2006.01) |
| A61K 9/06 | (2006.01) |
| A61K 9/20 | (2006.01) |
| A61K 9/70 | (2006.01) |
| A61K 31/473 | (2006.01) |
| A61K 47/02 | (2006.01) |
| A61K 47/10 | (2017.01) |
| A61K 47/18 | (2017.01) |

(52) U.S. Cl.
CPC ............ *A61K 31/485* (2013.01); *A61K 9/006* (2013.01); *A61K 9/0056* (2013.01); *A61K 9/06* (2013.01); *A61K 9/2086* (2013.01); *A61K 9/7007* (2013.01); *A61K 31/473* (2013.01); *A61K 47/02* (2013.01); *A61K 47/10* (2013.01); *A61K 47/183* (2013.01); *Y10T 428/2982* (2015.01)

(58) Field of Classification Search
CPC .... A61K 31/485; A61K 9/0056; A61K 9/006; A61K 9/06; A61K 9/2086; A61K 9/7007; A61K 31/473; A61K 47/02; A61K 47/10; A61K 47/183; Y10T 428/2982
See application file for complete search history.

(56) References Cited

U.S. PATENT DOCUMENTS

| | | |
|---|---|---|
| 1,234,123 A | 7/1917 | Bond |
| 3,972,995 A | 8/1976 | Tsuk et al. |
| 4,614,545 A | 9/1986 | Hess |
| 5,047,244 A | 9/1991 | Sanvordeker et al. |
| 5,441,747 A | 8/1995 | de Haan et al. |
| 5,523,090 A | 6/1996 | Znaiden et al. |
| 5,560,932 A | 10/1996 | Bagchi et al. |
| 5,624,677 A | 4/1997 | El-Rashidy et al. |
| 5,629,003 A | 5/1997 | Horstmann et al. |
| 5,700,478 A | 12/1997 | Biegajski et al. |
| 5,888,534 A | 3/1999 | El-Rashidy et al. |
| 5,945,117 A | 8/1999 | El-Rashidy et al. |
| 5,994,363 A | 11/1999 | El-Rashidy et al. |
| 6,087,362 A | 7/2000 | El-Rashidy |
| 6,121,276 A | 9/2000 | El-Rashidy et al. |
| 6,159,498 A | 12/2000 | Tapolsky et al. |
| 6,177,096 B1 | 1/2001 | Zerbe et al. |
| 6,193,992 B1 | 2/2001 | El-Rashidy et al. |
| 6,200,983 B1 | 3/2001 | El-Rashidy et al. |
| 6,264,981 B1 | 7/2001 | Zhang et al. |
| 6,284,264 B1 | 9/2001 | Zerbe et al. |
| 6,306,437 B1 | 10/2001 | El-Rashidy et al. |
| 6,316,027 B1 | 11/2001 | Johnson et al. |
| 6,375,963 B1 | 4/2002 | Repka et al. |
| 6,486,207 B2 | 11/2002 | Yeager et al. |
| 6,488,953 B2 | 12/2002 | Halliday et al. |
| 6,552,024 B1 | 4/2003 | Chen et al. |
| 6,566,368 B2 | 5/2003 | El-Rashidy et al. |
| 6,667,056 B2 | 12/2003 | Chiesi et al. |
| 6,756,407 B2 | 6/2004 | Heaton et al. |
| 6,974,590 B2 | 12/2005 | Pather et al. |
| 7,037,526 B1 | 5/2006 | Krumme et al. |
| 7,087,240 B1 | 8/2006 | Fotinos |
| 7,332,230 B1 | 2/2008 | Krumme |
| 7,357,891 B2 | 4/2008 | Yang et al. |
| 7,374,782 B2 | 5/2008 | Brown |
| 7,425,292 B2 | 9/2008 | Yang et al. |
| 7,579,019 B2 | 8/2009 | Tapolsky et al. |
| 7,666,337 B2 | 2/2010 | Yang et al. |

(Continued)

FOREIGN PATENT DOCUMENTS

| | | |
|---|---|---|
| AU | 746373 B2 | 4/2002 |
| CA | 02274893 A1 | 6/1998 |

(Continued)

OTHER PUBLICATIONS

Van Laar et al. Mov. Disord. 1996; 11(6): abstract.*

(Continued)

Primary Examiner — David Browe
(74) Attorney, Agent, or Firm — Clark & Elbing LLP; Kristina Bieker-Brady

(57) ABSTRACT

Disclosed are methods of treating Parkinson's disease by (i) providing a pharmaceutical composition in unit dosage form that is a film having a first portion including apomorphine particles containing an acid addition salt of apomorphine and a second portion containing a pH neutralizing agent, where the film contains the acid addition salt of apomorphine in an amount effective to treat Parkinson's disease, and (ii) administering the film by placing the film sublingually in the mouth of the subject and contacting sublingual mucosal tissue with the film.

22 Claims, No Drawings

(56) References Cited

U.S. PATENT DOCUMENTS

| | | | |
|---|---|---|---|
| 7,824,588 | B2 | 11/2010 | Yang et al. |
| 7,897,080 | B2 | 3/2011 | Yang et al. |
| 7,910,031 | B2 | 3/2011 | Yang et al. |
| 7,910,641 | B2 | 3/2011 | Myers |
| 8,017,150 | B2 | 9/2011 | Yang et al. |
| 8,414,922 | B2 | 4/2013 | Bryson et al. |
| 8,603,514 | B2 | 12/2013 | Yang et al. |
| 8,652,378 | B1 | 2/2014 | Yang et al. |
| 8,658,201 | B2 | 2/2014 | Singh et al. |
| 8,663,687 | B2 | 3/2014 | Myers et al. |
| 8,685,437 | B2 | 4/2014 | Yang et al. |
| 8,765,167 | B2 | 7/2014 | Myers et al. |
| 8,846,074 | B2 | 9/2014 | Bryson et al. |
| 9,044,475 | B2 | 6/2015 | Giovinazzo et al. |
| 2001/0006677 | A1 | 7/2001 | McGinity et al. |
| 2003/0022912 | A1* | 1/2003 | Martino ............... A61K 9/0043 514/292 |
| 2003/0073715 | A1 | 4/2003 | El-Rashidy et al. |
| 2003/0096012 | A1* | 5/2003 | Besse ................. A61K 9/006 424/489 |
| 2003/0107149 | A1 | 6/2003 | Yang et al. |
| 2004/0028613 | A1 | 2/2004 | Quay |
| 2004/0204440 | A1 | 10/2004 | Staniforth et al. |
| 2005/0031677 | A1 | 2/2005 | Pather et al. |
| 2005/0037055 | A1 | 2/2005 | Yang et al. |
| 2005/0226823 | A1 | 10/2005 | Krumme et al. |
| 2006/0141032 | A1* | 6/2006 | Larsen ................ A61K 9/0007 424/466 |
| 2006/0198873 | A1 | 9/2006 | Chan et al. |
| 2006/0210610 | A1 | 9/2006 | Davidson et al. |
| 2007/0149479 | A1 | 6/2007 | Fischer et al. |
| 2007/0149731 | A1 | 6/2007 | Myers |
| 2008/0008753 | A1 | 1/2008 | Singh |
| 2008/0057087 | A1 | 3/2008 | Krumme |
| 2008/0119504 | A1 | 5/2008 | Wikstrom et al. |
| 2008/0124381 | A1 | 5/2008 | Barnhart et al. |
| 2009/0023766 | A1 | 1/2009 | Clarke |
| 2010/0035886 | A1 | 2/2010 | Cincotta et al. |
| 2011/0033542 | A1 | 2/2011 | Myers et al. |
| 2011/0111011 | A1 | 5/2011 | Giovinazzo et al. |
| 2012/0195955 | A1 | 8/2012 | Bryson et al. |
| 2013/0064822 | A1 | 3/2013 | Ye et al. |
| 2013/0337148 | A1 | 12/2013 | Yang et al. |
| 2014/0377329 | A1 | 12/2014 | Bryson et al. |
| 2015/0216859 | A1 | 8/2015 | Giovinazzo et al. |
| 2016/0081914 | A1 | 3/2016 | Giovinazzo et al. |
| 2016/0089328 | A1 | 3/2016 | Giovinazzo et al. |
| 2016/0089367 | A1 | 3/2016 | Giovinazzo et al. |
| 2016/0095851 | A1 | 4/2016 | Giovinazzo et al. |
| 2016/0338972 | A1 | 11/2016 | Bryson et al. |

FOREIGN PATENT DOCUMENTS

| | | |
|---|---|---|
| CN | 1271276 A | 10/2000 |
| DE | 19652268 A1 | 6/1998 |
| JP | 2001-506612 A | 5/2001 |
| JP | 2002-531393 A | 9/2002 |
| JP | 2004-520389 A | 7/2004 |
| JP | 2004-534839 A | 11/2004 |
| JP | 2004-535361 A | 11/2004 |
| JP | 2005-263704 A | 9/2005 |
| JP | 2006-508060 A | 3/2006 |
| JP | 2007-517053 A | 6/2007 |
| JP | 2008-540392 A | 11/2008 |
| JP | 2009-521532 A | 6/2009 |
| JP | 5760295 B2 | 8/2015 |
| KR | 2000-0057627 A | 9/2000 |
| KR | 2008-0016608 A | 2/2008 |
| RU | 2189226 C2 | 9/2002 |
| RU | 2283650 C1 | 9/2006 |
| WO | WO-93/25168 A1 | 12/1993 |
| WO | WO-96/41619 A1 | 12/1996 |
| WO | WO-97/06786 A1 | 2/1997 |
| WO | WO-98/26763 A1 | 6/1998 |
| WO | WO-98/48781 A1 | 11/1998 |
| WO | WO-00/32171 A2 | 6/2000 |
| WO | WO-00/42992 A2 | 7/2000 |
| WO | WO-02/056808 A1 | 7/2002 |
| WO | WO-02/062315 A1 | 8/2002 |
| WO | WO-02/100377 A1 | 12/2002 |
| WO | WO-03/000018 A2 | 1/2003 |
| WO | WO-03/005944 A1 | 1/2003 |
| WO | WO-2004/026309 A1 | 4/2004 |
| WO | WO-2004/045537 A2 | 6/2004 |
| WO | WO-2004/066986 A1 | 8/2004 |
| WO | WO-2005/018323 A1 | 3/2005 |
| WO | WO-2005/065318 A2 | 7/2005 |
| WO | WO-2006/031209 A1 | 3/2006 |
| WO | WO-2006/039264 A1 | 4/2006 |
| WO | WO-2006/120412 A1 | 11/2006 |
| WO | WO-2007/030754 A2 | 3/2007 |
| WO | WO-2007/067494 A1 | 6/2007 |
| WO | WO-2007/075422 A2 | 7/2007 |
| WO | WO-2008/011194 A2 | 1/2008 |
| WO | WO-2008/039737 A2 | 4/2008 |
| WO | WO-2008/040534 A2 | 4/2008 |
| WO | WO-2008/100375 A2 | 8/2008 |
| WO | WO-2009/052421 A1 | 4/2009 |
| WO | WO-2010/144817 A1 | 12/2010 |
| WO | WO-2011/143424 A1 | 11/2011 |

OTHER PUBLICATIONS

"R-(-)-Apomorphine hydrochloride hemihydrate, calcined," <http://www.sigmaaldrich.com/content/dam/sigma-aldrich/docs/Sigma/Product_Information_Sheet/a4393pis.pdf>, accessed on Oct. 26, 2015 (1 page).

Communication enclosing the Extended European Search Report for European Patent Application No. 10786915.8, dated Oct. 12, 2012 (7 pages).

Declaration of Dr. Nathan Bryson Under 37 C.F.R. § 1.132 Traversing Grounds of Rejection for U.S. Appl. No. 12/813,820, dated Mar. 24, 2013 (6 pages).

English translation of Indonesian Substantive Examination Report Stage I for Indonesian Application No. W00201103305, Issued Jun. 5, 2014 (1 page).

English translation of Office Action for Japanese Patent Application No. 2012-515185, date mailed on Jul. 8, 2014 (3 pages).

Eurasian Search Report for Eurasian Application No. 201270012, dated Jun. 25, 2012 (3 pages).

Extended European Search Report for European Application No. 15175258.1, dated Oct. 19, 2015 (8 pages).

International Search Report and Written Opinion for International Patent Application No. PCT/US11/65665, mailed Apr. 23, 2012 (18 pages).

Koller et al., "Other formulations and future considerations for apomorphine for subcutaneous injection therapy," Neurology. 62(6 Suppl 4):S22-S26 (2004).

Lees et al., "Sublingual apomorphine and Parkinson's disease," J Neurol Neurosurg Psychiatry 52(12):1440 (1989) (2 pages).

Montastruc et al., "Sublingual apomorphine in Parkinson's disease: a clinical and pharmacokinetic study," Clin Neuropharmacol. 14(5):432-437 (1991).

Notice of Reasons for Rejection for Japanese Application No. 2012-515185, mailed Jul. 8, 2014 (6 pages).

Office Action for Israeli Application No. 216923 including English summary, mailed Dec. 1, 2015 (5 pages).

Office Action for Israeli Application No. 216923 including English summary, mailed Oct. 2, 2014 (6 pages).

Office Action for Korean Application No. 10-2012-7000835, dated Jun. 26, 2014 (English Translation included) (11 pages).

Office Action for Korean Application No. 10-2015-7016545, dated Oct. 6, 2015 (5 pages).

Official Action for Eurasian Application No. 201270012, dated Nov. 9, 2015 (3 pages).

Official Action for Eurasian Application No. 201270012, dated Oct. 9, 2013 (4 pages).

(56) References Cited

OTHER PUBLICATIONS

Ribaric, "The pharmacological properties and therapeutic use of apomorphine," Molecules. 17(5):5289-309 (2012).
Sanchez et al., "Interplay of chromatographic parameters and analyte physical properties on retention and selectivity in hydrophilic interaction liquid chromatography," Phenomenex, Inc., (2007) (18 pages).
Tan et al., "Functional COMT variant predicts response to high dose pyridoxine in Parkinson's disease," Am J Med Genet B Neuropsychiatr Genet. 137B(1):1-4 (2005).
Tsai et al., "Oral apomorphine delivery from solid lipid nanoparticles with different monostearate emulsifiers: pharmacokinetic and behavioral evaluations," J Pharm Sci. 100(2):547-557 (2011).
van Laar et al., "A new sublingual formulation of apomorphine in the treatment of patients with Parkinson's disease," Mov Disord. 11(6):633-8 (1996).
Weast (ed.), *CRC Handbook of Chemistry and Physics 52nd Edition*. The Chemical Rubber Company (1971) (p. D-119).
Design and Evaluation of Oral Administration Formulations, 1995, p. 199 (2 pages).
Notice of Reasons for Rejection for Japanese Application No. 2015-104145, mailed Apr. 19, 2016 (5 pages).
Extended European Search Report for European Application No. 15175258.1, mailed Oct. 19, 2015 (8 pages).
Office Action for U.S. Appl. No. 14/962,806, mailed Jun. 16, 2016 (13 pages).
Office Action for U.S. Appl. No. 14/963,835, mailed Jun. 17, 2016 (11 pages).
Office Action for U.S. Appl. No. 14/963,910, mailed Jun. 23, 2016 (15 pages).
Office Action for U.S. Appl. No. 14/963,971, mailed Jun. 21, 2016 (16 pages).
Trial Decision for Korean Application No. 2012-7000835, mailed Jul. 28, 2016 (19 pages).
Official Action for Japanese Application No. 2016-047759, mailed Jan. 31, 2017 (4 pages).
Ondo et al., "Novel sublingual apomorphine treatment for patients with fluctuating Parkinson's disease," Movement Disorders. 14(4):664-8 (1999).
Semalty et al., "Formulation and characterization of mucoadhesive buccal films of glipizide," Indian J Pharm Sci. 70(1):43-8 (2008).
del Consuelo, "Ex vivo evaluation of bioadhesive films for buccal delivery of fentanyl," J Control Release. 122(2):135-40 (2007).
Ying Kin et al., "Stability of apomorphine hydrochloride in aqueous sodium bisulphite solutions," Prog Neuropsychopharmacol Biol Psychiatry. 25(7):1461-8 (2001).
Sam et al., "Stability of apomorphine in plasma and its determination by high-performance liquid chromatography with electrochemical detection," J Chromatogr B Biomed Appl. 658(2):311-7 (1994).
Goswami et al., "Sublingual drug delivery," Crit Rev Ther Drug Carrier Syst. 25(5):449-84 (2008).
Harris et al., "Drug delivery via the mucous membranes of the oral cavity," J Pharm Sci. 81(1):1-10 (1992).
Chapter 9: Basic Biopharmaceutics of Buccal and Sublingual Absorption and Chapter 10: Chemical Enchancers in Buccal and Subligual Absorptions. Enhancement in Drug Delivery Touitou and Barry, 175-213 (2007) (22 pages).
Gandhi et al., "Oral cavity as a site for bioadhesive drug delivery," Adv Drug Deliv Rev. 13(1-2):43-74 (1994).
Chapter 55: Pharmaceutical Necessities and Chapter 57: Drug Absorption, Action, and Dispositon. Remington: The Science and Practice of Pharmacy. Gennaro, 1015, 1098-1126 (2000) (33 pages).
Notice of Opposition for European Patent No. EP2442650, dated May 27, 2016 (37 pages).
Notice of Opposition for European Patent No. EP2442650, dated May 26, 2016 (25 pages).
Summons to attend oral proceedings pursuant to Rule 115(1) EPC for European Patent No. 2442650, dated Mar. 20, 2017 (15 pages).

"Cynapsus Receives FDA Fast Track Designation for APL-130277 for the Treatment of OFF Episodes in Patients with Parkinson's Disease," Globe Newswire, available <https://globenewswire.com/news-release/2016/08/29/867552/0/en/Cynapsus-Receives-FDA-Fast-Track-Designation-for-APL-130277-for-the-Treatment-of-OFF-Episodes-in-Patients-with-Parkinson-s-Disease.html>, dated Aug. 29, 2016 (3 pages).
"Fast Track," available <http://www.fda.gov/ForPatients/Approvals/Fast/ucm405399.htm>, accessed Oct. 28, 2016 (2 pages).
"Sunovion Pharmaceuticals to Acquire Cynapsus Therapeutics," dated Aug. 31, 2016 (6 pages).
Ahlskog et al., "Frequency of levodopa-related dyskinesias and motor fluctuations as estimated from the cumulative literature," Mov Disord. 16(3):448-58 (2001).
APO-go Ampoules 10mg/ml Package Leaflet, Feb. 2013 (2 pages).
Apokyn Prescribing information, Britannia Pharmaceuticals Limited, available <http://www.apokyn.com/assets/APOKYN_PI.pdf>, 2004 (16 pages).
Aquino et al., "Clinical spectrum of levodopa-induced complications," Mov Disord. 30(1):80-9 (2015).
Arny, The Pyridine and Quinoline Derivatives. *Principles of Pharmacy*. W. B. Saunders, p. 823 (1917).
Bhidayasiri et al., "Effective delivery of apomorphine in the management of Parkinson disease: practical considerations for clinicians and Parkinson nurses," Clin Neuropharmacol. 38(3):89-103 (2015).
Chapuis et al., "Impact of the motor complications of Parkinson's disease on the quality of life," Mov Disord. 20(2):224-30 (2005).
Cotzias et al., "Similarities between neurologic effects of L-dopa and of apomorphine," N Engl J Med. 282(1):31-3 (1970).
Declaration of Dr. Nathan Bryson Under 37 C.F.R. § 1.132 Traversing Grounds of Rejection for U.S. Appl. No. 13/445,656, dated Sep. 24, 2012 (10 pages).
HBM Pharma/Biotech M&A Report 2016, Jan. 2016 (16 pages).
Holloway et al., "Pramipexole vs levodopa as initial treatment for Parkinson disease: a 4-year randomized controlled trial," Arch Neurol. 61(7):1044-53 (2004) (11 pages).
Hornykiewicz, "Basic research on dopamine in Parkinson's disease and the discovery of the nigrostriatal dopamine pathway: the view of an eyewitness," Neurodegener Dis. 5(3-4):114-7 (2008).
López et al., "Motor complications in Parkinson's disease: ten year follow-up study," Mov Disord. 25(16):2735-9 (2010).
Michael J Fox Foundation, MJFF Off Time Survey, "Executive Summary: Survey of Parkinson's Patients and Their Off Time Experience" (2 pages).
Michael J Fox Foundation, MJFF Survey—OFF Time Survey Results, "Impact of Parkinson's Disease Off Episodes," Aug. 11, 2014 (13 pages).
Notice of Allowance for U.S. Appl. No. 13/445,656, mailed Dec. 13, 2012 (17 pages).
Notice of Allowance for U.S. Appl. No. 13/858,638, mailed Aug. 8, 2014 (23 pages).
Notice of Allowance for U.S. Appl. No. 14/478,975, mailed Nov. 3, 2015 (32 pages).
Notice of Allowance for U.S. Appl. No. 15/014,655, mailed Jul. 19, 2016 (34 pages).
Notice of Final Rejection for Korean Application No. 10-2015-7016545, mailed Sep. 5, 2016 (8 pages).
Oertel et al., "Pergolide versus levodopa monotherapy in early Parkinson's disease patients: The PELMOPET study," Mov Disord 21(3):343-53 (2006).
Office Action for Japanese Application No. 2015-104145, mailed Dec. 6, 2016 (2 pages).
Office Action for U.S. Appl. No. 13/858,638, mailed Jul. 3, 2013 (10 pages).
Office Action for U.S. Appl. No. 13/858,638, mailed Sep. 6, 2013 (22 pages).
Olanow et al., "Factors predictive of the development of Levodopa-induced dyskinesia and wearing-off in Parkinson's disease," Mov Disord. 28(8):1064-71 (2013).
Ondo et al., "Apomorphine injections: predictors of initial common adverse events and long term tolerability," Parkinsonism Relat Disord. 18(5):619-22 (2012).

(56) References Cited

OTHER PUBLICATIONS

Rascol et al., "A five-year study of the incidence of dyskinesia in patients with early Parkinson's disease who were treated with ropinirole or levodopa," N Engl J Med. 342(20):1484-91 (2000).
Reply to Office Action for U.S. Appl. No. 13/445,656, dated Sep. 24, 2012 (18 pages).
Reply to Office Action for U.S. Appl. No. 13/858,638, dated Feb. 6, 2014 (10 pages).
Response to Office Action for U.S. Appl. No. 13/853,290, mailed Mar. 24, 2016 (17 pages).
Response to Restriction Requirement for U.S. Appl. No. 13/858,638, dated Aug. 1, 2013 (1 page).
Rizos et al., "Characterizing motor and non-motor aspects of early-morning off periods in Parkinson's disease: an international multicenter study," Parkinsonism Relat Disord. 20(11):1231-5 (2014).
Supplemental Amendment for U.S. Appl. No. 13/445,656, dated Nov. 20, 2012 (5 pages).
Tanner et al., "Epidemiology of Parkinson's disease," Neurol Clin. 14(2):317-35 (1996).
Wüllner et al., "Requirements for Parkinson's disease pharmacotherapy from the patients' perspective: a questionnaire-based survey," Curr Med Res Opin. 28(7):1239-46 (2012).

\* cited by examiner

SUBLINGUAL APOMORPHINE

STATEMENT UNDER 35 U.S.C. §103(c)(2)(C)

The claimed invention was made as a result of activities undertaken within the scope of a joint research agreement between Adagio Pharmaceuticals Ltd. and Cynapsus Therapeutics, Inc.

BACKGROUND OF THE INVENTION

The invention relates to compositions including apomorphine, or an apomorphine prodrug, and formulated for sublingual administration and the use of such compositions for the treatment of Parkinson's disease.

Parkinson's disease (PD) is a progressive degenerative disease of the central nervous system. The risk of developing Parkinson's disease increases with age, and afflicted individuals are usually adults over 40. Parkinson's disease occurs in all parts of the world, and affects more than 1.5 million individuals in the United States alone.

While the primary cause of Parkinson's disease is not known, it is characterized by degeneration of dopaminergic neurons of the substantia nigra. The substantia nigra is a portion of the lower brain, or brain stem that helps control voluntary movements. The shortage of dopamine in the brain caused by the loss of these neurons is believed to cause the observable disease symptoms.

The symptoms of PD vary from patient to patient. The most common symptom is a paucity of movement and rigidity, characterized by an increased stiffness of voluntary skeletal muscles. Additional symptoms include resting tremor, bradykinesia (slowness of movement), poor balance, and walking problems. Common secondary symptoms include depression, sleep disturbance, dizziness, stooped posture, dementia, problems with speech, breathing, and swallowing. The symptoms become progressively worse with time and ultimately result in death.

A variety of therapeutic treatments for PD are available. Perhaps the best known is levodopa, a dopamine precursor. While levodopa administration can result in a dramatic improvement in symptoms, patients can experience serious side-effects, including nausea and vomiting. Concurrent carbidopa administration with levodopa is a significant improvement, with the addition of carbidopa inhibiting levodopa metabolism in the gut, liver and other tissues, thereby allowing more levodopa to reach the brain. Other dopamine agonists, such as bromocriptine, pergolide, pramipexole, and andropinirole are also used to treat Parkinson's disease, and can be administered to PD patients either alone or in combination with levodopa.

Many patients develop involuntary choreiform movements which are the result of excessive activation of dopamine receptors. These movements usually affect the face and limbs and can become very severe. Such movements disappear if the dose of dopamine precursor (e.g., levodopa) or dopamine agonist is reduced, but this typically causes rigidity to return. Moreover, the margin between the beneficial and the unwanted effects appear to become progressively narrower as the period of chemotherapeutic treatment lengthens.

A further complication of long-term chemotherapeutic treatment with dopamine agonists is the development of rapid fluctuations in clinical state where the patient switches suddenly between mobility and immobility for periods ranging from a few minutes to a few hours. The fluctuations are of several general types. "Wearing-off" phenomena are deteriorations in the relief afforded by a dose of levodopa before the next dose takes effect (Van Laar T., CNS Drugs, 17:475 (2003)). Because they are related to a patient's dose schedule, such periods are often relatively predictable (Dewey R B Jr., Neurology, 62(suppl 4):S3-S7 (2004)). In contrast, "on-off" phenomena are sudden transitions from an "on" period of levodopa benefit to an "off" period of akinesia, rigidity, and tremor that occur in minutes or even seconds, (Swope D M., Neurology, 62(suppl 4):S27-S31 (2004)) with no discernible relation to a patient's dose schedule. Two other phenomena are the delayed "on" effect, in which levodopa's effects are substantially delayed, and dose failure (also known as the no-"on" or skipped-dose effect), in which no effects occur at all. These various "off" states can produce such an abrupt loss of mobility that the patient may suddenly stop while walking or be unable to rise from a chair in which he had sat down normally a few moments earlier.

Subcutaneous injections of apomorphine have proved to be effective in the treatment of "on-off" fluctuations in Parkinson's disease within 5 to 15 minutes, and last for 45 to 90 minutes. Trials have shown consistent reversal of "off" period akinesia, a decrease in daily levodopa requirements and consequently a decrease in the amount of "on" period dyskinesias. Advantages over other dopamine agonists include a quick onset of action and lower incidence of psychological complications. For a "rescue therapy" in patients with "on-off" fluctuations, apomorphine also has the advantage over other dopamine agonists that it has a relatively short half-life.

Numerous formulations and routes of administration for apomorphine have been studied and apomorphine therapy has been found to be hampered by various complications. For example, oral administration of apomorphine tablets has required high doses to achieve the necessary therapeutic effect because apomorphine administered by this route undergoes extensive metabolism in the small intestine and/or, upon absorption, in the liver; sublingual administration of apomorphine tablets caused severe stomatitis on prolonged use with buccal mucosal ulceration in half the patients treated (see Deffond et al., J. Neurol. Neurosurg. Psychiatry 56:101 (1993)); and intranasal administration produced transient nasal blockage, burning sensation and swollen nose and lips (see Koller et al., Neurology 62:S22 (2004)). While subcutaneous injections of apomorphine have proven effective, an injection by needle is difficult for Parkinson's patients because of impaired motor function. Furthermore, a common side effect of subcutaneous injection is the development of nodules, which often become infected, necessitating antibiotic treatment or surgical debridement (see Prietz et al., J. Neurol. Neurosurg. Psychiatry 65:709 (1998)).

There is a need for new formulations of apomorphine and apomorphine prodrugs which are safe, effective, and easy for a Parkinson's patient to use.

SUMMARY OF THE INVENTION

The invention features sublingual formulations of apomorphine and apomorphine prodrugs. The formulations can be useful for the treatment of Parkinson's disease, sexual dysfunction, and depressive disorders therewith.

In a first aspect, the invention features a pharmaceutical composition in unit dosage form (e.g., a lozenge, a pill, a tablet, a film, or a strip) formulated for sublingual administration, the unit dosage form having a first portion including an acid addition salt of apomorphine, or an apomorphine prodrug, and a second portion including a pH neutralizing agent (e.g., polyamines, calcium hydroxide, magnesium hydroxide, potassium hydroxide, sodium hydroxide, calcium carbonate, iron carbonate, magnesium carbonate, zinc carbonate, sodium acetate, sodium carbonate, potassium carbonate, sodium bicarbonate, potassium bicarbonate, sodium phosphate monobasic, sodium phosphate dibasic, sodium phosphate tribasic, potassium phosphate monobasic, potassium phosphate dibasic, potassium phosphate tribasic, and mixtures thereof, or any other suitable base).

In certain embodiments, the unit dosage form is a film or a strip and wherein the unit dosage form includes a mucoadhesive polymer. The mucoadhesive polymer can be, without limitation, any mucoadhesive polymer described herein.

In one particular embodiment, the acid addition salt of apomorphine, or an apomorphine prodrug, is apomorphine hydrochloride. In another particular embodiment, the acid addition salt of apomorphine, or an apomorphine prodrug, is protonated apomorphine complexed to an anionic polyelectrolyte or protonated apomorphine prodrug complexed to an anionic polyelectrolyte (e.g., alginates, carrageenan, xanthan gum, polyacrylate, or carboxymethylcellulose).

In still another embodiment, the pharmaceutical composition is a film or a strip, wherein the first portion is a first layer and the second portion is a second layer, the first layer being acidic and including the acid addition salt of apomorphine, or an apomorphine prodrug, and the second layer including the pH neutralizing agent.

In certain embodiments, the sublingual formulation includes an antioxidant. The antioxidant can be, without limitation, any antioxidant described herein.

In particular embodiments, the sublingual formulation includes a first portion that is a film including a solid solution of an acid addition salt of apomorphine, or an apomorphine prodrug, and includes a second portion that is a particulate base on or within the unit dosage form. The particulate base can include, for example, sodium carbonate, potassium carbonate, sodium bicarbonate, potassium bicarbonate, sodium phosphate monobasic, sodium phosphate dibasic, sodium phosphate tribasic, potassium phosphate monobasic, potassium phosphate dibasic, potassium phosphate tribasic, or a mixture thereof.

In still another embodiment, the first portion of the unit dosage form is separated from the second portion of the unit dosage form by a barrier (e.g., a film separating an acidic layer from a basic layer in a multi-layered film, or a coating on a particulate base or apomorphine particle contained within the unit dosage form). The barrier can be neutral in pH (e.g., between 6 and 7.8), separating the acidic first portion from the basic second portion of the unit dosage form.

In a related aspect, the invention features a pharmaceutical composition formulated for sublingual administration including apomorphine particles having an effective particle size of from 20 nm to 10 μm, wherein the apomorphine particles include apomorphine, an apomorphine prodrug, or a salt thereof.

In certain embodiments, the pharmaceutical composition is in a unit dosage form selected from a lozenge, a pill, a tablet, a film, or a strip. In other embodiments, the pharmaceutical composition is a sublingual gel.

The sublingual formulations can include apomorphine particles having an effective particle size of from 1 μm to 10 μm (e.g., an effective particle size of from 1 μm to 9 μm, from 1 μm to 8 μm, from 1 μm to 7 μm, from 1 μm to 6 μm, from 1 μm to 5 μm, from 2 μm to 10 μm, from 3 μm to 10 μm, from 4 μm to 10 μm, from 2 μm to 7 μm, or from 2 μm to 6 μm).

In certain other embodiments, the sublingual formulations can include apomorphine particles having an effective particle size of from 20 nm to 1 μm (e.g., an effective particle size of from 20 nm to 1 μm, from 40 nm to 1 μm, from 60 nm to 1 μm, from 80 nm to 1 μm, from 100 nm to 1 μm, from 20 nm to 800 nm, from 20 nm to 700 nm, from 50 nm to 700 nm, from 40 nm to 800 nm, from 60 nm to 800 nm, from 100 nm to 800 nm, from 60 nm to 700 nm, from 60 nm to 600 nm, from 100 nm to 600 nm, from 150 nm to 800 nm, or from 150 nm to 600 nm).

In still other embodiments, the sublingual formulation includes a mucoadhesive polymer. The mucoadhesive polymer can be, without limitation, any mucoadhesive polymer described herein.

In certain embodiments, the sublingual formulation includes apomorphine particle and the apomorphine particle include an acid addition salt of apomorphine or an apomorphine prodrug. The acid addition salt can be apomorphine hydrochloride or any acid addition salt described herein. Alternatively, the acid addition salt can be the hydrochloride salt of an apomorphine prodrug or any other acid addition salt described herein.

In a particular embodiment, the sublingual formulation in unit dosage form is a film or a strip including a mucoadhesive polymer. The mucoadhesive polymer can be, without limitation, any mucoadhesive polymer described herein. For example, the film or strip can include a first layer and a second layer, the first layer being acidic and including the apomorphine particles and the second layer including a pH neutralizing agent (e.g., polyamines, calcium hydroxide, magnesium hydroxide, potassium hydroxide, sodium hydroxide, calcium carbonate, iron carbonate, magnesium carbonate, zinc carbonate, sodium acetate, sodium carbonate, potassium carbonate, sodium bicarbonate, potassium bicarbonate, sodium phosphate monobasic, sodium phosphate dibasic, sodium phosphate tribasic, potassium phosphate monobasic, potassium phosphate dibasic, potassium phosphate tribasic, and mixtures thereof, or any other suitable base).

In certain embodiments, the sublingual formulation includes an antioxidant. The antioxidant can be, without limitation, any antioxidant described herein.

In another aspect, the invention features a pharmaceutical composition formulated for sublingual administration including protonated apomorphine, or an apomorphine prodrug, complexed to an anionic polyelectrolyte (e.g., alginates, carrageenan, xanthan gum, polyacrylate, or carboxymethylcellulose). In certain embodiments, the sublingual formulation includes an antioxidant. The antioxidant can be, without limitation, any antioxidant described herein.

In particular embodiments, the pharmaceutical composition is in a unit dosage form selected from a lozenge, a pill, a tablet, a film, or a strip. In still other embodiments, the pharmaceutical composition is a sublingual gel.

In another aspect, the invention features a pharmaceutical composition in unit dosage form formulated for sublingual administration, the unit dosage form including from 2 to 50 mg of an apomorphine prodrug (e.g., from 2 to 15 mg, 10 to 50 mg, 12 to 30 mg, 20 to 50 mg, 15 to 30 mg, or 35 to 50 mg of an apomorphine prodrug). In particular embodiments, the unit dosage form is a lozenge, a pill, a tablet, a film, or strip including from the apomorphine prodrug in its free base form. In still other embodiments, the unit dosage form is a lozenge, a pill, a tablet, a film, or strip including a solid solution of the apomorphine prodrug in its free base form.

In an embodiment of any of the above pharmaceutical compositions, the pharmaceutical composition is in a unit dosage form including from 2 to 40 mg of apomorphine, an apomorphine prodrug, or an acid addition salt thereof (e.g., from 2 to 5 mg, 4 to 10 mg, 6 to 15 mg, 8 to 20 mg, 10 to 25 mg, 12 to 30 mg, 20 to 35 mg, 25 to 40 mg, or 30 to 40 mg of apomorphine, an apomorphine prodrug, or an acid addition salt thereof). For example, each unit dosage form can contain 3±1 mg, 4±1 mg, 5±1 mg, 8±2 mg, 10±3 mg, 12±3 mg, 15±3 mg, 22±4 mg, 27±4 mg, 30±5 mg, 35±5 mg, or 40±5 mg of apomorphine, an apomorphine prodrug, or an acid addition salt thereof.

In another embodiment of any of the above pharmaceutical compositions, the unit dosage form when placed in 1 mL of unbuffered water at pH 7 results in a solution having a pH of between 7.4 and 9.1 (e.g., a pH of between 7.4 and 8.8, 7.4 and 8.3, 7.6 and 8.8, 7.6 and 8.5, 8.2 and 8.5, 8.4 and 8.7, 8.6 and 8.8, or 8.7 and 9.1).

In still another embodiment of any of the above pharmaceutical compositions, following sublingual administration to a subject the unit dosage form produces an average circulating concentration of at least 3 ng/mL within a period of from 5 to 15 minutes following the administration. For example, the unit dosage form can produce an average circulating concentration of from 3 to 6 ng/mL within 7 to 10 minutes, from 5 to 10 ng/mL within 5 to 10 minutes, from 7 to 12 ng/mL within 5 to 10 minutes, from 10 to 16 ng/mL within 5 to 10 minutes, from 3 to 6 ng/mL within 7 to 15 minutes, from 5 to 10 ng/mL within 7 to 15 minutes, from 7 to 12 ng/mL within 7 to 15 minutes, from 10 to 16 ng/mL within 7 to 15 minutes, from 3 to 6 ng/mL within 15 to 20 minutes, from 5 to 10 ng/mL within 15 to 20 minutes, from 7 to 12 ng/mL within 15 to 20 minutes, or from 10 to 16 ng/mL within 15 to 20 minutes following the administration.

The invention further features a method of treating Parkinson's disease in a mammal by sublingually administering a pharmaceutical composition of the invention to the mammal in an amount effective to treat the mammal.

The invention also features a method for alleviating dyskinesia in a mammal afflicted with Parkinson's disease by sublingually administering a pharmaceutical composition of the invention to the mammal in an amount effective to alleviate the dyskinesia.

The invention also features a method for alleviating akinesia in a mammal afflicted with Parkinson's disease by sublingually administering a pharmaceutical composition of the invention to the mammal in an amount effective to alleviate the akinesia.

The invention features a method of treating sexual dysfunction in a mammal by sublingually administering a pharmaceutical composition of the invention to the mammal in an amount effective to treat the mammal.

The invention also features a method of treating a depressive disorder in a mammal by sublingually administering a pharmaceutical composition of the invention to the mammal in an amount effective to treat the mammal.

In one embodiment of any of the above methods, the method further includes administration of an effective amount of an anti-emetic agent (e.g., nicotine, lobeline sulfate, pipamazine, oxypendyl hydrochloride, ondansetron, buclizine hydrochloride, cyclizine hydrochloride, dimenhydrinate, scopolamine, metopimazine, benzauinamine hydrochloride, or diphenidol hydrochloride).

In embodiment of any of the above methods and compositions, the apomorphine, apomorphine prodrug, or salt thereof is a racemic mixture of R and S isomers, or enriched in R isomer (i.e., the ratio of R to S isomer for all of the apomorphine in the composition, or all the apomorphine being administered, is from 5:1 to 1,000:1, from 10:1 to 10,000:1, or from 100:1 to 100,000:1, or over all apomorphine isomers in the composition is at least 98% R isomer, 99% R isomer, 99.5% R isomer, 99.9% R isomer, or is free of any observable amount of S isomer.

The term "administration" or "administering" refers to a method of giving a sublingual dosage of apomorphine, or an apomorphine prodrug, to a patient.

As used herein, the term "apomorphine particle" refers to microparticles or nanoparticles containing apomorphine, an apomorphine prodrug, or salts thereof.

As used herein, the term "average circulating concentration" refers to the average plasma concentration of apomorphine at time t observed for a group of subjects following sublingual administration of a particular unit dosage form of the invention. For example, among 20 subjects the average circulating concentration concentration of apomorphine 10 minutes following sublingual administration of the unit dosage form can be at least 3 ng/mL, 5 ng/mL, 7 ng/mL, 9 ng/mL, 11 ng/mL, 13 ng/mL, or 15 ng/mL, depending upon the amount of apomorphine in the unit dosage.

By "depressive disorder" is meant any psychological or psychiatric disorder associated with symptoms of depressed mood. Treatable depressive disorders may be characterized by an inhibition or reduction of dopaminergic function in the nucleus accumbens, e.g., major depression, dysthymia, bipolar disorder (manic depression), and post-traumatic stress disorder.

As used herein, the terms "effective particle size" and "particle size" are used interchangeably and refer to a mixture of particles having a distribution in which 50% of the particles are below and 50% of the particles are above a defined measurement. The "effective particle size" refers to the volume-weighted median diameter as measured by a laser/light scattering method or equivalent, wherein 50% of the particles, by volume, have a smaller diameter, while 50% by volume have a larger diameter. The effective particle size can be measured by conventional particle size measuring techniques well known to those skilled in the art. Such techniques include, for example, sedimentation field flow fractionation, photon correlation spectroscopy, light scattering (e.g., with a Microtrac UPA 150), laser diffraction, and disc centrifugation.

As used herein, the term "apomorphine prodrug" refers to apomorphine esters and glycosides of formula (I):

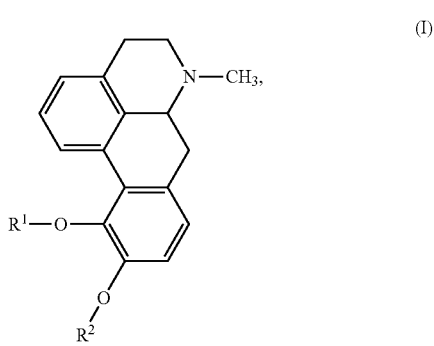

and acid addition salts thereof. In formula I, each of $R^1$ and $R^2$ is, independently, H, C(O)—$R_3$, C(O)—O—$R_3$, or a glycoside of a monosaccharide or oligosaccharide; or $R^1$ and $R^2$ combine with the oxygen atoms to which they are bound to form a cyclic acetal, cyclic ketal, a cyclic carbonate (i.e., —C(O)—O—C(O)—), or an orthoester glycoside; and $R_3$ is a cyclic, straight chained, or branched hydrocarbon of 1 to 12 carbon atoms, which is optionally saturated (i.e., a $C_{1-12}$ alkyl), includes one or more carbon-carbon double bonds (i.e., a $C_{2-12}$ alkenyl), and/or includes one or more carbon-carbon triple bonds (i.e., a $C_{2-12}$ alkynyl). For example, the apomorphine glycosides can be glycosides of straight or branched chain glycosidic moiety containing 1-20 glycosidic units. Apomorphine glycosides and orthoester glycosides can be synthesized as described in PCT Publication No. WO/2003/080074. Apomorphine esters, cyclic acetals, and cyclic ketals can be synthesized using methods analogous to those described in U.S. Pat. No. 4,687,773, Borgman et al., J. Med. Chem., 19:717 (1976), and PCT Publication No. WO/2005/099702. The above patent publications are incorporated herein by reference. Carbonate esters of apomorphine can be prepared as described in Atkinson et al., J. Pharma. Sci. 65:1685 (1976), and in Campbell et al., Neuropharmacology 21:953 (1982). Apomorphine prodrugs which can be used in the unit dosage forms of the invention include, without limitation, O,O'-diacetylapomorphine, O,O'-dipropionylapomorphine, O,O'-diisobutyrylapomorphine, O,O'-dipivaloylapomorphine, O,O'-dibenzoylapomorphine, apomorphine carbonate, apomorphine diethylcarbonate, apomorphine methylene acetal, apomorphine ethyl acetal, apomorphine dimethyl acetal, and acid addition salts thereof.

As used herein, "pH neutralizing agent" refers to any basic component present in the unit dosage forms of the invention. The pH neutralizing agents which can be used in the unit dosage forms of the invention include organic bases (e.g., amines), inorganic bases (e.g., oxides, hydroxides, carbonates, or phosphates), and mixtures thereof. The pH neutralizing agent is typically present in an amount sufficient to produce a solution having a pH of between 7.4 and 9.1 when the unit dosage form is placed in 1 mL of unbuffered water at pH 7.

As used herein, "sexual dysfunction" refers to disorders of orgasm, response timing, ejaculation, nociception, congestive arousal and erection, vasculogenic impairment, or desire. In males, the form of sexual dysfunction is typically erectile dysfunction, the inability to achieve and sustain an erection sufficient for intercourse. Females also can have sexual dysfunctions of arousal and orgasm that increase with age and are associated with the presence of vascular risk factors and onset of menopause. Some of the vascular and muscular mechanisms that contribute to penile erection in the male are believed to involve similar vasculogenic factors in female genital responses. Female sexual dysfunction includes a failure to attain or maintain vaginal lubrication-swelling responses of sexual excitement until completion of the sexual activity.

As used herein, the term "treating" refers to administering a pharmaceutical composition for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease to ameliorate the disease and improve the patient's condition. Thus, in the claims and embodiments, treating is the administration to a mammal either for therapeutic or prophylactic purposes.

Other features and advantages of the invention will be apparent from the following detailed description and the claims.

DETAILED DESCRIPTION

The invention features sublingual formulations of apomorphine and apomorphine prodrugs. The formulations can be useful for the treatment of Parkinson's disease, sexual dysfunction, and depressive disorders therewith. In certain aspects, the invention features (i) sublingual formulations in unit dosage form having a first portion including an acid addition salt of apomorphine, or an apomorphine prodrug, and a second portion including a pH neutralizing agent; (ii) sublingual formulations including apomorphine particles having an effective particle size of from 20 nm to 10 µm; and/or (iii) sublingual formulations including protonated apomorphine, or an apomorphine prodrug, complexed to an anionic polyelectrolyte.

Fluctuations in motor disability and dyskinesias are a significant problem in the long-term treatment of Parkinson's disease. In the later stages of Parkinson's disease, many patients develop severe "off" episodes where, despite continuing to take their medication, they experience periods when they lose the ability to move (e.g., the patients develop bradykinesia (slowed movement) or akinesia (inability to move)). These "off" episodes typically occur 3 to 4 times per day.

Apomorphine has a rapid onset of action which is ideal for use as a rescue therapy for intractable "off" periods in Parkinson's disease.

Using the sublingual formulations of the invention, a subject suffering from the effects of middle stage or late stage Parkinson's disease may be able to recognize the onset of their "off" symptoms and be capable of administering a sublingual dose of a formulation of the invention to alleviate the dyskinesia associated with such "off" episodes. The sublingual formulations are easy for a subject with compromised motor skills to administer and can relieve a Parkinson's patient from the need for a caregiver, who might otherwise be needed to administer an injectable dosage form of apomorphine at the onset of an "off" episode.

The sublingual formulations of the invention can increase the bioavailability of apomorphine, prolong the stability of apomorphine, and/or improve the safety and efficacy of apomorphine therapy. The formulations can produce a rapid uptake of apomorphine into the subject, allowing dyskinesia episodes to be self-treated. Furthermore, the convenience with which these sublingual formulations can be self administered provides a significant advantage to severely ill patients, such as those with middle stage or late stage Parkinson's disease.

Additional details of how to make and use the sublingual formulations of the invention are provided below and in the Examples.

Monolayer and Bilayer Films

The films of the invention are not dissimilar to the films used, for example, to make the Listerine® PocketPak® mouth fresheners. In PocketPak films the polymers used are typically polysaccharide-based or polysaccharide and glycoprotein-based gums such as pullulan, pectin, locust bean gum, xanthan gum, sodium alginate, gum Arabic and the like. These same polymers can be used in the films of the invention.

The films can include one layer, two layers, or more. If in two layers, the one adapted to adhere to mucosal tissue may be referred to as the "adhesive layer." With two layers, the outer layer can be less adhesive or non-adhesive, and can provide protection against mechanical agitation, such as agitation by a user's tongue. The components of the outer layer might be, of themselves, less dissolvable than the components of an adhesive layer. However, in the aggregate, the film shall dissolve in that it will transition to fully dissolved parts or parts that will be carried away by normal cleaning processes at the mucosal tissue in question. In forming two layers, diffusion or the forming process itself may provide a gradient in component amounts in the transition between the two layers. The two layers can be utilized to separate components (e.g., an apomorphine-containing, or an apomorphine prodrug-containing, acidic layer and a buffered pH neutralizing layer), which together enhance absorption of the apomorphine, or apomorphine prodrug, but are otherwise incompatible in a formulation requiring long term stability (i.e., shelf life). Alternatively, the unit dosage form of the invention can be a monolayer film that is an apomorphine-containing, or an apomorphine prodrug-containing, acidic layer which is coated with or impregnated with a particulate base. The particulate base can be incorporated into the monolayer film using the methods described in PCT Publication No. WO/2009/052421, U.S. Patent Publication No. 20060210610, each of which is incorporated herein by reference. The film of the invention can include an effervescent particulate (i.e., a particulate carbonate base). Such effervescent films can be prepared as described in U.S. Patent Publication No. 20010006677, incorporated herein by reference.

The polymers used in the films of the invention can be polymers that affect the rate of hydration or mucosal adhesion properties of an adhesive layer. Such polymers can be, for example, carboxymethylcellulose, cellulose acetate, ethylcellulose, hydroxyethylcellulose, hydroxypropylmethylcellulose (HPMC, such as Pharmacoat 606™, Shin-Etsu Chemical Company Ltd., Japan), nitrocellulose, polyoxyethylene/polyoxypropylene polymers, copolymers or block copolymers, polyvinylpyrrolidone polymers or derivatives, and gums. The average molecular weight of the polymer can be selected based on the swelling and dissolution profile sought. Mixtures of less soluble and/or less swellable polymers with more soluble or swellable polymers can help transition the film to a sufficiently dissolved form. For example, the film can include carbamer, polyethylene oxide, ethylcellulose, titanium oxide and colorant (such as F, D and C blue lake colorant). Often the film is formed using a pharmaceutically appropriate solvent such as ethanol, water, mixtures, or the like. Such solvents are typically largely evaporated away prior to use. Optionally, the films comprise a blend of more than one polymers or more than one molecular weight of a given set of polymers in order to control the rate of hydration, physical properties and mechanical properties.

Basic Layers

The multi-layered films of the invention can include a film formed from a basic polymer. Polyamines which can be used in the unit dosage forms of the invention include homo and copolymers of dimethylaminoethyl-acrylate, dimethylaminoethyl-methacrylate, dimethylaminopropyl-acrylate, dimethylaminpropyl-methacrylate, or other similar amino-functionalized acrylate, chitosan or partially hydrolyzed chitin in a substantially basic form, homo and co polymers of polyethyleimine, polylysine, polyvinylimidazole, or polyvinylamine. In certain embodiments the polyamine is Eudragit E100.

Other Components

Plasticizers, penetration enhancers, flavoring agents, preservatives, odorants, coloring agents, and the like can be included in the unit dosage forms of the invention.

Plasticizers will generally modify the feel, softness, flexibility (in an un-wetted state) of the unit dosage forms of the invention. Penetration enhancers may, in some cases, act as plasticizers. Examples of plasticizers include, without limitation, glycerol, propylene glycol, fatty acid esters, such as glyceryl oleate, polyalcohols, sorbitan esters, citric acid esters, polyethylene glycol (e.g., PEG 400), polyvinyl alcohol, polyvinyl methyl ether, triacetin; mannitol, xylitol, and sorbitol. The plasticizer can be present in any suitable range, including, for example about 0.5% to 30%, 10% to 20%, or 15% to 18% by weight of the dry film.

Permeation enhancers can be used to improve the permeability of the apomorphine at the mucosal membrane in the unit dosage forms of the invention. One or more permeation enhancers maybe used to modulate the rate of mucosal absorption of the apomorphine. Any effective permeation enhancers may be used including, for example, bile salts, such as sodium cholate, sodium glycocholate, sodium glycodeoxycholate, taurodeoxycholate, sodium deoxycholate, sodium lithocholate chenocholate, chenodeoxycholate, ursocholate, ursodeoxy-cholate, hyodeoxycholate, dehydrocholate, glycochenocholate, taurochenocholate, and taurochenodeoxycholate; sodium dodecyl sulfate (SDS), dimethyl sulfoxide (DMSO), N-lauroyl sacrcosine, sorbitan monolaurate, stearyl methacrylate, N-dodecylazacycloheptan-2-one, N-dodecyl-2-pyrrolidinone, N-dodecyl-2-piperidinone, 2-(1-nonyl)-1,3-dioxolane, N-(2-methoxymethyl) dodecylamine, N-dodecylethanolamine, N-dodecyl-N-(2-methoxymethyl)acetamide, 1-N-dodecyl-2-pyrrolidone-5-carboxylic acid, 2-pentyl-2-oxo-pyrrolidineacetic acid, 2-dodecyl-2-oxo-1-pyrrolidineacetic acid, 2-dodecyl-2-oxo-1-pyrrolidineacetic acid, 1-azacylioheptan-2-one-dodecylacetic acid, menthol, propylene glycol, glycerol monostearate, sorbitol monolaurate, glycerol dilaurate, tocopherol acetate, phosphatidyl choline, glycerol, polyethyleneglycol, monoglycerides, diglycerides, triglycerides, lecithin, tween surfactants, sorbitan surfactants, sodium lauryl sulfate; salts and other derivatives of saturated and unsaturated fatty acids, surfactants, bile salt analogs, derivatives of bile salts, or such synthetic permeation enhancers as described in U.S. Pat. No. 4,746,508, which is incorporated herein by reference.

A flavoring agent and/or odorant can be added to the unit dosage forms of the invention to make them more palatable. At least one flavoring agent or odorant composition may be used. Any effective flavor or odor may be rendered. The flavoring agents may be natural, artificial, or a mixture thereof. The flavoring agent gives a flavor that is attractive to the user. In one embodiment, the flavoring agent may give the flavor of mint, honey lemon, orange, lemon lime, grape, cranberry, vanilla berry, Magnasweet™, bubble gum, or cherry. The flavoring agent can be natural or artificial sweetener, such as sucrose, xylitol, sodium saccharin, cyclamate, aspartame, acesulfame, and salts thereof.

Apomorphine is susceptible to oxidative degradation. To minimize oxidative degradation it is desirable that the formulations of the invention contain one or more antioxidants. Antioxidants that can be used in the films of the invention can be selected from thiols (e.g., aurothioglucose, dihydrolipoic acid, propylthiouracil, thioredoxin, glutathione, cysteine, cystine, cystamine, thiodipropionic acid), sulphoximines (e.g., buthionine-sulphoximines, homo-cysteine-sulphoximine, buthionine-sulphones, and penta-, hexa- and heptathionine-sulphoximine), metal chelators (e.g, α-hydroxy-fatty acids, palmitic acid, phytic acid, lactoferrin, citric acid, lactic acid, and malic acid, humic acid, bile acid, bile extracts, bilirubin, biliverdin, EDTA, EGTA, and DTPA), sodium metabisulfite, vitamins (e.g., vitamin E, vitamin C, ascorbyl palmitate, Mg ascorbyl phosphate, and ascorbyl acetate), phenols (e.g., butylhydroxytoluene, butylhydroxyanisole, ubiquinol, nordihydroguaiaretic acid, trihydroxybutyrophenone), benzoates (e.g., coniferyl benzoate), uric acid, mannose, propyl gallate, selenium (e.g., seleniummethionine), stilbenes (e.g., stilbene oxide and trans-stilbene oxide), and combinations thereof. The total amount of antioxidant included in the films can be from 0.001% to 3% by weight, preferably 0.01% to 1% by weight, in particular 0.05% to 0.5% by weight, based on the total weight of the formulation.

In certain embodiments, the various components (e.g., plasticizers, penetration enhancers, flavoring agents, preservatives, odorants, coloring agents, particulate base, and apomorphine particles) included in the unit dosage forms of the invention can be combined and incorporated into a first portion that is acidic and includes the apomorphine, or a prodrug thereof, or combined and incorporated into a second portion that is basic and includes a pH neutralizing component, or the components may be divided between the two portions. In some instances it may be desirable to minimize interaction between the acidic portion of the unit dosage form and the basic portion of the unit dosage form by including a barrier between the two. For example, a barrier can be included in the unit dosage forms of the invention as a third layer interposed between the acidic layer and the basic layer of a multilayer sublingual dosage form. Alternatively, the barrier can be a rapidly dissolving coating on the surface of a particulate component in the unit dosage form, such as a coated particulate base coated onto, or embedded within, an acidic portion of the unit dosage form. In still another approach, the barrier can be a rapidly dissolving coating on the surface of apomorphine particles in the unit dosage form, which further includes a basic portion. These approaches can be utilized to ensure that the apomorphine-containing, or an apomorphine prodrug-containing, acidic portion of the unit dosage form is not neutralized prior to the administration to a subject.

Apomorphine Particles

The pharmaceutical formulations described herein can include apomorphine particles having an effective particle size of from about 1 micron to about 10 microns. The starting apomorphine composition can be predominantly crystalline, predominantly amorphous, or a mixture thereof, and can include unmodified apomorphine or an apomorphine prodrug.

In an alternative approach, the pharmaceutical formulations described herein can include apomorphine particles having an effective particle size of less than about 1 micron (i.e., nanoparticulate formulations). The starting apomorphine composition can be predominantly crystalline, predominantly amorphous, or a mixture thereof, and can include unmodified apomorphine or an apomorphine prodrug.

These apomorphine particles can be made by using any method known in the art for achieving the desired particle sizes. Useful methods include, for example, milling, homogenization, supercritical fluid fracture, or precipitation techniques. Exemplary methods are described in U.S. Pat. Nos. 4,540,602; 5,145,684; 5,518,187; 5,718,388; 5,862,999; 5,665,331; 5,662,883; 5,560,932; 5,543,133; 5,534,270; and 5,510,118; 5,470,583, each of which is specifically incorporated by reference.

Milling to Obtain Submicron Apomorphine Particles

In one approach, the apomorphine, an apomorphine prodrug, or a salt thereof, is milled in order to obtain micron or submicron particles. The milling process can be a dry process, e.g., a dry roller milling process, or a wet process, i.e., wet-grinding. A wet-grinding process is described in U.S. Pat. Nos. 4,540,602, 5,145,684, 6,976,647 and EPO 498,482, the disclosures of which are hereby incorporated by reference. Thus, the wet grinding process can be practiced in conjunction with a liquid dispersion medium and dispersing or wetting agents such as described in these publications. Useful liquid dispersion media include safflower oil, ethanol, n-butanol, hexane, or glycol, among other liquids selected from known organic pharmaceutical excipients (see U.S. Pat. Nos. 4,540,602 and 5,145,684), and can be present in an amount of 2.0-70%, 3-50%, or 5-25% by weight based on the total weight of the apomorphine, or apomorphine prodrug, in the formulation.

The grinding media for the particle size reduction step can be selected from rigid media, typically spherical in shape, though non-spherical grinding media could also be used. The grinding media preferably can have a mean particle size from 1 mm to about 500 microns. For fine grinding, the grinding media particles can have a mean particle size from about 0.05 to about 0.6 mm. Smaller size grinding media will result in smaller size apomorphine particles as compared to the same conditions using larger sized grinding media. In selecting material, grinding media with higher density, e.g., glass (2.6 g/cm$^3$), zirconium silicate (3.7 g/cm$^3$), and zirconium oxide (5.4 g/cm$^3$) and 95% zirconium oxide stabilized with yttrium, can be utilized for more efficient milling. Alternatively, polymeric grinding media can be used. Polymeric resins suitable for use herein are chemically and physically inert, substantially free of metals, solvent and monomers, and of sufficient hardness and friability to enable them to avoid being chipped or crushed during grinding. Suitable polymeric resins include, without limitation, crosslinked polystyrenes, such as polystyrene crosslinked with divinylbenzene, styrene copolymers, polycarbonates, polyacetals, such as Delrin™, vinyl chloride polymers and copolymers, polyurethanes, polyamides, poly (tetrafluoroethylenes), e.g., Teflon™, and other fluoropolymers, high density polyethylenes, polypropylenes, cellulose ethers and esters such as cellulose acetate, polyhydroxymethacrylate, polyhydroxyethyl acrylate, and silicone containing polymers such as polysiloxanes.

Grinding can take place in any suitable grinding mill. Suitable mills include an airjet mill, a roller mill, a ball mill, an attritor mill, a vibratory mill, a planetary mill, a sand mill and a bead mill. A high energy media mill is preferred when small particles are desired. The mill can contain a rotating shaft.

The preferred proportions of the grinding media, apomorphine or apomorphine prodrug, the optional liquid dispersion medium, and dispersing, wetting or other particle stabilizing agents present in the grinding vessel can vary within wide limits and depend on, for example, the size and density of the grinding media, the type of mill selected, the time of milling, etc. The process can be carried out in a continuous, batch or semi-batch mode. In high energy media mills, it can be desirable to fill 80-95% of the volume of the grinding chamber with grinding media. On the other hand, in roller mills, it frequently is desirable to leave the grinding vessel up to half filled with air, the remaining volume comprising the grinding media and the liquid dispersion media, if present. This permits a cascading effect within the vessel on the rollers which permits efficient grinding. However, when foaming is a problem during wet grinding, the vessel can be completely filled with the liquid dispersion medium or an anti-foaming agent may be added to the liquid dispersion.

The attrition time can vary widely and depends primarily upon the mechanical means and residence conditions selected, the initial and desired final particle size, among other factors. For roller mills, processing times from several days to weeks may be required. On the other hand, milling residence times of less than about 2 hours are generally required using high energy media mills. After attrition is completed, the grinding media is separated from the milled apomorphine particulate product (in either a dry or liquid dispersion form) using conventional separation techniques, such as by filtration, or sieving through a mesh screen.

To produce apomorphine particles having an effective particle size of less than about 1 micron, the grinding media can be made from beads having a size ranging from 0.05 mm to 4 mm. For example, high energy milling of apomorphine, or an apomorphine prodrug, with yttrium stabilized zirconium oxide 0.4 mm beads for a milling residence time of 25 minutes to 1.5 hours in recirculation mode at 1200 to 3000 RPM. In another approach, high energy milling of apomorphine, or an apomorphine prodrug, with 0.1 mm zirconium oxide balls for a milling residence time of 2 hours in batch mode can be used. The milling concentration can be from about 10% to about 30% apomorphine, or apomorphine prodrug, by weight in comparison to the milling slurry weight, which can contain a wetting and/or dispersing agent to coat the initial suspension so a uniform feed rate may be applied in continuous milling mode. Alternatively, batch milling mode is utilized with a milling media containing an agent to adjust viscosity and/or provide a wetting effect so that the apomorphine, or apomorphine prodrug, is well dispersed amongst the grinding media.

Microprecipitation to Obtain Apomorphine Nanoparticles

Apomorphine particles can also be prepared by homogeneous nucleation and precipitation in the presence of a wetting agent or dispersing agent using methods analogous to those described in U.S. Pat. Nos. 5,560,932 and 5,665,331, which are specifically incorporated by reference. Such a method can include the steps of: (1) dispersing apomorphine, or an apomorphine prodrug, in a suitable liquid media; (2) adding the mixture from step (1) to a mixture including at least one dispersing agent or wetting agent such that at the appropriate temperature, the apomorphine, or an apomorphine prodrug, is dissolved; and (3) precipitating the formulation from step (2) using an appropriate anti-solvent. The method can be followed by removal of any formed salt, if present, by dialysis or filtration and concentration of the dispersion by conventional means. In one embodiment, the apomorphine particles are present in an essentially pure form and dispersed in a suitable liquid dispersion media. In this approach the apomorphine particles are a discrete phase within the resulting mixture. Useful dispersing agents, wetting agents, solvents, and anti-solvents can be experimentally determined.

Homogenization to Obtain Apomorphine Nanoparticles

Apomorphine particles can also be prepared by high pressure homogenization (see U.S. Pat. No. 5,510,118). In this approach apomorphine particles are dispersed in a liquid dispersion medium and subjected to repeated homogenization to reduce the particle size of the apomorphine particles to the desired effective average particle size. The apomorphine particles can be reduced in size in the presence of at least one or more dispersing agents or wetting agents. Alternatively, the apomorphine particles can be contacted with one or more dispersing agents or wetting agents either before or after attrition. Other materials, such as a diluent, can be added to the apomorphine/dispersing agent mixture before, during, or after the size reduction process. For example, unprocessed apomorphine, or an apomorphine prodrug, can be added to a liquid medium in which it is essentially insoluble to form a premix (i.e., about 0.1-60% w/w apomorphine, or apomorphine prodrug, and about 20-60% w/w dispersing agents or wetting agents). The apparent viscosity of the premix suspension is preferably less than about 1000 centipoise. The premix can then be transferred to a microfluidizer and circulated continuously first at low pressures, and then at maximum capacity (i.e., 3,000 to 30,000 psi) until the desired particle size reduction is achieved. The resulting dispersion of apomorphine particles can be spray coated onto a sublingual pharmaceutical formulation of the invention using techniques well known in the art.

Milling with Simethicone

Foaming during the nanosizing can present formulation issues and can have negative consequences for particle size reduction. For example, high levels of foam or air bubbles in the mill can cause a drastic increase in viscosity rendering the milling process inoperable. Even a very low level of air presence can dramatically reduce milling efficiency causing the desired particle size unachievable. This may be due to the resultant air in the mill cushioning the milling balls and limiting grinding efficiency. The air also can form a microemulsion with the milled ingredients which presents many issues with respect to the delivery of an accurate dose and palatability. Addition of a small amount of simethicone is a very effective anti-foaming agent which minimizes milling variability or special handling techniques to avoid the introduction of air into the milling process.

The Use of Wetting and Dispersing Agents

The apomorphine particles can be prepared with the use of one or more wetting and/or dispersing agents, which are, e.g., adsorbed on the surface of the apomorphine particle. The apomorphine particles can be contacted with wetting and/or dispersing agents either before, during or after size reduction. Generally, wetting and/or dispersing agents fall into two categories: non-ionic agents and ionic agents. The most common non-ionic agents are excipients which are contained in classes known as binders, fillers, surfactants and wetting agents. Limited examples of non-ionic surface stabilizers are hydroxypropylmethylcellulose, polyvinylpyrrolidone, Plasdone, polyvinyl alcohol, Pluronics, Tweens and polyethylene glycols (PEGs). Ionic agents are typically organic molecules bearing an ionic bond such that the molecule is charged in the formulation, such as long chain sulfonic acid salts (e.g., sodium lauryl sulfate and dioctyl sodium sulfosuccinate).

Excipients, such as wetting and dispersing agents, can be applied to the surface of the apomorphine nanoparticulate via spray drying, spray granulation, or spray layering process. These procedures are well known in those skilled in the art. It is also common to add additional excipients prior to removal of solvent in the nanoparticulate suspension to aid in the dispersion of the solid composition in medium in which the solid composition will be exposed (e.g. saliva) to further prevent agglomeration and/or particle size growth of the small apomorphine particles. An example of such an additional excipient is a redispersing agent. Suitable redispersing agents include, without limitation, sugars, polyethylene glycols, urea and quarternary ammonium salts.

Therapy

Representative examples of diseases and conditions treatable using the sublingual formulations of the invention are as listed hereinabove, and include, but are not limited to, Parkinson's disease, sexual dysfunction, and depressive disorders, such as major depression and bipolar disorder.

Sublingual formulations of the invention include rapidly disintegrating or dissolving dosage forms, also known as fast dissolve, fast or rapid melt, and quick disintegrating dosage forms. These dosage forms dissolve or disintegrate rapidly in the patient's mouth without chewing or the need for water within a short time frame. Because of their ease of administration, such compositions are particularly useful for the specific needs of patients with compromised motor skills. The sublingual formulations may be in unit dosage form in the shape of, for example, a lozenge, a pill, a tablet, a film, or a strip. Alternatively, the sublingual formulations may be prepared in non-unit dosage forms, such as a gel.

The apomorphine, or apomorphine prodrug, may be administered in its free base form or as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, alginic acid, or the like; and inorganic acid such as hydrochloric acid, hydrobromic acid, sulfuric acid phosphoric acid, or the like. Metal complexes include calcium, zinc, iron, and the like. In certain instances the formulation of the invention includes apomorphine hydrochloride, or the hydrochloride salt of or an apomorphine prodrug.

The formulations can be administered to patients in therapeutically effective amounts. For example, an amount is administered which prevents, reduces, or eliminates the symptoms of Parkinson's disease, sexual dysfunction, or depression, respectively. Typical dose ranges are from about 2 mg to about 30 mg of apomorphine, or a salt thereof, given up to five times per day. The exemplary dosage of apomorphine, or apomorphine prodrug, to be administered is likely to depend on such variables as the type and extent of the condition, the overall health status of the particular patient, the particular form of apomorphine being administered, and the particular sublingual formulation being used.

Potential adverse effects can be ameliorated by administering apomorphine, or an apomorphine prodrug, in combination with an anti-emetic agent, such as nicotine, lobeline sulfate, pipamazine, oxypendyl hydrochloride, ondansetron, buclizine hydrochloride, cyclizine hydrochloride, dimenhydrinate, scopolamine, metopimazine, benzauinamine hydrochloride or diphenidol hydrochloride. In certain instances it may be desirable to incorporate the anti-emetic into the sublingual formulation for simultaneous administration in combination with apomorphine, or apomorphine prodrug.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Example 1—Two Layer Apomorphine Strip

Preparation of the First Layer:

Gelatin and mannitol are dispersed in purified water and mixed thoroughly (i.e., using a vacuum mixer) and homogenized. Apomorphine hydrochloride is added and the mixture was again homogenized to ensure complete dissolution of the apomorphine hydrochloride. The pH of the solution is adjusted to about 3.0 (i.e., by addition of a suitable acid, such as citric acid). The solution is then poured onto a sheet and dried in a heated oven.

Preparation of the Second Layer:

Ethyl cellulose, poly(ethylene oxide), and hydroxypropylcellulose are dissolved in anhydrous ethanol. To the resulting solution is added a pH modifying agent (i.e., calcium hydroxide, magnesium hydroxide, potassium hydroxide, sodium hydroxide, calcium carbonate, iron carbonate, magnesium carbonate, zinc carbonate, sodium acetate, sodium carbonate, potassium carbonate, sodium bicarbonate, potassium bicarbonate, sodium phosphate monobasic, sodium phosphate dibasic, sodium phosphate tribasic, potassium phosphate monobasic, potassium phosphate dibasic, potassium phosphate tribasic, and mixtures thereof). Alternatively, the pH modifying agent can be a polyamine, such as Eudragit E100.

A solvent-cast mucoadhesive film is prepared by casting a thin film of the solution onto the first layer. Evaporation of the solvent (ethanol) can be accomplished by drying at 60° C. for 30 minutes.

The resultant dry film includes (i) a first acidic layer containing apomorphine in a stable acid addition salt form (i.e., the hydrochloride salt), and (ii) a second basic layer (the adhesive layer) capable of neutralizing some of the apomorphine at the time of sublingual administration. The two layer film can enhance the bioavailability of the apomorphine, as absorption is enhanced when apomorphine hydrochloride is neutralized, without compromising the shelf life stability of the film.

The two-layer film is cut into strips, each strip containing the equivalent of from 2 mg to 20 mg of apomorphine in its free base form. The strips can be administered to a subject for the treatment of Parkinson's disease, sexual dysfunction, or depressive disorders.

Example 2—Single Layer Nanoparticulate Apomorphine Strip

Ethyl cellulose, poly(ethylene oxide), and hydroxypropylcellulose are dissolved in anhydrous ethanol to form a solution.

Nanoparticulate apomorphine hydrochloride is prepared by milling solid apomorphine hydrochloride as described herein.

The particulate apomorphine is suspended in the solution and a solvent-cast mucoadhesive film is prepared by casting a thin film of the mixture onto a sheet. Evaporation of the solvent (ethanol) can be accomplished by drying at 60° C. for 30 minutes.

The resultant dry film includes a single adhesive layer that releases nanoparticulate apomorphine. The apomorphine can penetrate the mucosal tissue in its nanoparticulate form, thus enhancing the bioavailability of the apomorphine in the film.

The single-layer nanoparticulate film is cut into strips, each strip containing the equivalent of from 2 mg to 20 mg of apomorphine in its free base form. The strips can be administered to a subject for the treatment of Parkinson's disease, sexual dysfunction, or depressive disorders.

Example 3—Single Layer Apomorphine Free Base Strip

All materials are degassed prior to use and all steps are carried out under a nitrogen atmosphere.

Ethyl cellulose, poly(ethylene oxide), and hydroxypropylcellulose are dissolved in anhydrous ethanol to form a polymer solution.

The apomorphine hydrochloride and an antioxidant (e.g., sodium metabisulfite) are dissolved in a minimal amount of water and added to the polymer solution. The pH of the resulting mixture is adjusted to about 9.0 (i.e., by addition of a suitable base, such as sodium hydroxide).

A solvent-cast mucoadhesive film is prepared by casting a thin film of the mixture onto a sheet. Evaporation of the solvent (ethanol/water) can be accomplished by drying at 60° C. for 30 minutes, and/or drying under reduced pressure.

The resultant dry film includes a single adhesive layer that releases free base apomorphine. The apomorphine can penetrate the mucosal tissue in its nanoparticulate form, thus enhancing the bioavailability of the apomorphine in the film.

The single-layer film is cut into strips, each strip containing the equivalent of from 2 mg to 20 mg of apomorphine in its free base form. The strips can be administered to a subject for the treatment of Parkinson's disease, sexual dysfunction, or depressive disorders.

Example 4—Two-Layer Apomorphine-Anionic Polyelectrolyte Complex

Preparation of the First Layer:

Apomorphine (free base) is combined with alginic acid to form an apomorphine-alginate complex. To the complex is added gelatin, mannitol, and purified water. The mixture is mixed thoroughly (i.e., using a vacuum mixer) and homogenized. The pH of the solution is adjusted to about 3.0. The solution is then poured onto a sheet and dried in a heated oven.

Preparation of the Second Layer:

Ethyl cellulose, poly(ethylene oxide), and hydroxypropyl cellulose are dissolved in anhydrous ethanol. To the resulting solution is added a pH modifying agent (i.e., calcium hydroxide, magnesium hydroxide, potassium hydroxide, sodium hydroxide, calcium carbonate, iron carbonate, magnesium carbonate, zinc carbonate, sodium acetate, sodium carbonate, potassium carbonate, sodium bicarbonate, potassium bicarbonate, sodium phosphate monobasic, sodium phosphate dibasic, sodium phosphate tribasic, potassium phosphate monobasic, potassium phosphate dibasic, potassium phosphate tribasic, and mixtures thereof). Alternatively, the pH modifying agent can be a polyamine, such as Eudragit E100.

A solvent-cast mucoadhesive film is prepared by casting a thin film of the solution onto the first layer. Evaporation of the solvent (ethanol) can be accomplished by drying at 60° C. for 30 minutes.

The resultant dry film includes (i) a first acidic layer containing apomorphine in a stable acid addition salt complex with alginic acid, and (ii) a second basic layer (the adhesive layer) capable of neutralizing some of the apomorphine at the time of sublingual administration. The two layer film can enhance the bioavailability of the apomorphine, as absorption is enhanced when apomorphine is neutralized, without compromising the shelf life stability of the film.

The two-layer film is cut into strips, each strip containing the equivalent of from 2 mg to 20 mg of apomorphine in its free base form. The strips can be administered to a subject for the treatment of Parkinson's disease, sexual dysfunction, or depressive disorders.

Example 5—Nanoparticulate Apomorphine Gel

Nanoparticulate apomorphine hydrochloride is prepared by milling solid apomorphine hydrochloride as described herein.

The particulate apomorphine is combined with sodium carboxymethylcellulose and glycerol. The resulting mixture is mixed thoroughly (i.e., using a vacuum mixer) and homogenized. Water is added to the mixture (with extensive mixing) to form a hydrogel containing suspended nanoparticles of apomorphine hydrochloride.

The nanoparticulate gel can be dispensed under the tongue in amounts containing the equivalent of from 2 mg to 20 mg of apomorphine in its free base form. The gel can be administered to a subject for the treatment of Parkinson's disease, sexual dysfunction, or depressive disorders.

Example 6—Apomorphine-Anionic Polyelectrolyte Complex Gel

Apomorphine (free base) is combined with alginic acid to form an apomorphine-alginate complex.

The apomorphine-alginate complex is combined with sodium carboxymethylcellulose, glycerol, and an antioxidant (e.g., sodium metabisulfite). The resulting mixture is mixed thoroughly (i.e., using a vacuum mixer) and homogenized. Water is added to the mixture (with extensive mixing) to form a hydrogel containing apomorphine-alginate complex.

The gel can be dispensed under the tongue in amounts containing the equivalent of from 2 mg to 20 mg of apomorphine in its free base form. The gel can be administered to a subject for the treatment of Parkinson's disease, sexual dysfunction, or depressive disorders.

Example 7—Bilayer Apomorphine with Polymer-Based Neutralizer

The following ingredients are mixed with 200 parts 2-1 water-ethanol solvent in an oxygen free environment: 40 parts apomorphine hydrochloride, 5 parts citric acid, 7 parts Methocel E5, 18 parts Methocel E50, 3 parts Klucel JF, 6 parts Sucralose, 3 parts PEG400, 3 parts sorbitol, 1 Prosweet G, 4 parts maltodextrin M180, 4 parts IPC B792, and 6 parts spearmint. The mixture is spread on a thin plastic liner and dried to produce a film of ca. 40 µm thickness.

Separately, Eudragit E100 is dissolved to form a viscous mixture in ethanol and acetone 1:1. The mixture is spread on a thin plastic liner to produce a film of ca. 24 µm thickness.

The apomorphine layer is fused to the Eudragit layer using heat (60° C.) and pressure to create a bilayer film. Individual dosing units of 40 mg apomorphine hydrochloride are obtained by cutting the film to 2.5×1 cm.

Example 8—Tablet with Apomorphine and Basic Agent

The following ingredients are blended: 40 parts apomorphine hydrochloride jet-milled to 10 µm (D95), 100 parts lactose, 100 parts microcrystalline cellulose, 5 parts sodium phosphate dibasic, 25 parts crosslinked povidone, 18 parts sucralose, 2 parts colloidal silica, 5 parts mint flavoring, and 5 parts magnesium stearate. Tablets of 300 mg are pressed to provide tablets containing 40 mg of apomorphine.

Alternatively, the present ingredients can be segregated into an apomorphine containing mixture and second, sodium phosphate mixture, which are pressed into a bilayer tablet.

Example 9—Dispersed Milled Apomorphine in Bilayer Thin Film

According to methods of a previous example, jet-milled powder of apomorphine hydrochloride (D95<10 µm) is added to a mixture of polyethyleneglycol, polyprrolidone, sucralose, sorbitol and xylitol in ethanol-ethylacetate to create a homogeneous dispersion of the active ingredient. The mixture is spread on a thin plastic liner and dried to produce a film of ca. 40 µm thickness. This film can be administered as is or combined with a neutralizing layer as per previous examples. Also contemplated, is the addition of jet-milled sodium carbonate to the dispersion of ingredient prior to drying to create a single layer wherein both active apomorphine hydrochloride and a neutralizing agent are dispersed as solid agents within a single layer.

Example 10—Hard Candy Lozenge

A candy matrix is formed by mixing one cup (240 grams) of sugar, ⅓ cup (81 cc) of light corn syrup, and slightly more than 1 cup (240 ml) of water. The matrix mixture is heated to a temperature of at least 285° F., taking care to avoid stirring the mixture at temperatures greater than 200° F. to prevent uncontrolled crystallization of the sugar mixture. The matrix mixture is allowed to cool to 260° F., and 4 ml of a flavoring agent and ⅛ teaspoon (0.625 cc) of citric acid are added, followed by the addition of 900 mg of milled apomorphine HCl and 1800 mg sodium phosphate dibasic. These ingredients are stirred thoroughly into the matrix, and the resulting mixture is poured into molds which have been sprayed with an anti-stick coating (e.g., sprayed with the anti-stick coating known under the trademark PAM). Sticks are inserted 2 minutes after pouring into the molds. Desirably, the hard candy lozenge is prepared under an inert atmosphere to minimize oxidation of the apomorphine.

It should be noted that the mixture contains no die, no alcohol, no synthetic flavor agents and no preservatives, and is completely natural.

Example 11—Monolayer Apomorphine with Particulate Base Neutralizer

The following ingredients are mixed with 200 parts 2-1 water-ethanol solvent in an oxygen free environment: 40 parts apomorphine hydrochloride, 5 parts citric acid, 7 parts Methocel E5, 18 parts Methocel E50, 3 parts Klucel JF, 6 parts Sucralose, 3 parts PEG400, 3 parts sorbitol, 1 Prosweet G, 4 parts maltodextrin M180, 4 parts IPC B792, and 6 parts spearmint. The mixture is spread on a thin plastic liner and dried to produce a film of ca. 40 µm thickness.

Separately, a pH neutralizing solid (e.g., sodium carbonate, potassium carbonate, sodium bicarbonate, potassium bicarbonate, sodium phosphate monobasic, sodium phosphate dibasic, sodium phosphate tribasic, potassium phosphate monobasic, potassium phosphate dibasic, potassium phosphate tribasic, or mixtures thereof) is milled to produce a microparticulate base. That the neutralizing solid is optionally coated with a neutral barrier, such as polyethylene glycol.

The apomorphine layer is coated with the microparticulate base, for example, by electrospray or static spray application. Optionally, the layer may be heated (ca. 60° C.) and the microparticulate base pressed into the apomorphine layer to form a monolayer film containing a solid solution of apomorphine hydrochloride with a microparticulate base dispersed within the film. Individual dosing units of 40 mg apomorphine hydrochloride are obtained by cutting the film to 2.5×1 cm.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of treating Parkinson's disease in a subject in need thereof, the method comprising:
   (i) providing a pharmaceutical composition in unit dosage form that is a film having a first portion comprising apomorphine particles comprising acid addition salt of apomorphine and a second portion comprising a pH neutralizing agent, wherein the film comprises the acid addition salt of apomorphine in an amount effective to treat Parkinson's disease; and
   (ii) administering the film by placing the film sublingually in the mouth of the subject and contacting sublingual mucosal tissue with the film.

2. The method of claim 1, wherein the acid addition salt of apomorphine is apomorphine hydrochloride.

3. The method of claim 1, wherein the film further comprises an antioxidant.

4. The method of claim 1, wherein the film further comprises a permeation enhancer.

5. The method of claim 1, wherein the film further comprises glycerol monostearate.

6. The method of claim 1, wherein the first portion comprises apomorphine particles having an effective particle size of from 1 µm to 10 µm.

7. The method of claim 1, wherein the film comprises a polysaccharide.

8. The method of claim 1, wherein the film comprises from 2 to 40 mg of an acid addition salt of apomorphine.

9. The method of claim 8, wherein the film comprises 12±3 mg of an acid addition salt of apomorphine.

10. The method of claim 8, wherein the film comprises 22±4 mg of an acid addition salt of apomorphine.

11. The method of claim 8, wherein the film comprises 30±5 mg of an acid addition salt of apomorphine.

12. The method of claim 8, wherein the film comprises 35±5 mg of an acid addition salt of apomorphine.

13. The method of claim 1, wherein the pH neutralizing agent is an organic base.

14. The method of claim 1, wherein following sublingual administration the film produces an average circulating apomorphine plasma concentration of at least 3 ng/mL within 20 minutes.

15. The method of claim 1, wherein the film comprises a mucoadhesive polymer.

16. The method of claim 8, wherein the film comprises 15±3 mg of an acid addition salt of apomorphine.

17. The method of claim 1, wherein said first portion is a first layer and said second portion is a second layer.

18. The method of claim 1, wherein said unit dosage form is a non-effervescent unit dosage form.

19. The method of claim 1, wherein the film comprises 12 to 30 mg of an acid addition salt of apomorphine.

20. The method of claim 19, wherein said acid addition salt of apomorphine is apomorphine hydrochloride.

21. The method of claim 17, wherein the film comprises 12 to 30 mg of an acid addition salt of apomorphine.

22. The method of claim 21, wherein said acid addition salt of apomorphine is apomorphine hydrochloride.

* * * * *